United States Patent
Hochman

(10) Patent No.: US 9,504,790 B1
(45) Date of Patent: Nov. 29, 2016

(54) DEVICE AND METHOD FOR IDENTIFICATION OF A TARGET REGION

(71) Applicant: Mark N. Hochman, New York, NY (US)

(72) Inventor: Mark N. Hochman, New York, NY (US)

(73) Assignee: MILESTONE SCIENTIFIC, INC., Livingston, NJ (US)

( * ) Notice: Subject to any disclaimer, the term of this patent is extended or adjusted under 35 U.S.C. 154(b) by 0 days.

(21) Appl. No.: 15/050,681

(22) Filed: Feb. 23, 2016

(51) Int. Cl.
*A61M 31/00* (2006.01)
*A61M 5/20* (2006.01)

(52) U.S. Cl.
CPC ........ *A61M 5/20* (2013.01); *A61M 2005/2013* (2013.01); *A61M 2205/13* (2013.01); *A61M 2205/3334* (2013.01); *A61M 2205/3344* (2013.01); *A61M 2205/52* (2013.01); *A61M 2205/581* (2013.01)

(58) Field of Classification Search
CPC ................. A61M 2205/334; A61M 2205/332; A61M 2025/0007; A61M 2202/048; A61M 5/46; A61M 5/1723; A61B 5/4896
See application file for complete search history.

(56) References Cited

U.S. PATENT DOCUMENTS

| | | | |
|---|---|---|---|
| 4,518,383 A | 5/1985 | Evans et al. | |
| 5,295,967 A | 3/1994 | Rondelet et al. | |
| 5,611,778 A | 3/1997 | Brinon | |
| 5,902,273 A | 5/1999 | Yang et al. | |
| 6,024,576 A | 2/2000 | Bevirt et al. | |
| 6,200,289 B1 | 3/2001 | Hochman et al. | |
| 6,773,417 B2 | 8/2004 | Fitzgibbons et al. | |
| 7,922,689 B2 | 4/2011 | Lechner | |
| 8,079,976 B2 | 12/2011 | Patrick et al. | |
| 8,137,312 B2 | 3/2012 | Sundar et al. | |
| 8,142,414 B2 | 3/2012 | Patrick et al. | |
| 8,197,443 B2 | 6/2012 | Sundar et al. | |
| 2002/0016567 A1 | 2/2002 | Hochman et al. | |
| 2002/0016569 A1 | 2/2002 | Critchlow et al. | |
| 2006/0122555 A1 | 6/2006 | Hochman | |
| 2008/0281265 A1 | 11/2008 | Hochman | |
| 2009/0326482 A1 | 12/2009 | Hochman | |
| 2011/0120566 A1 | 5/2011 | Ohmi et al. | |
| 2011/0298628 A1 | 12/2011 | Vad | |
| 2011/0301500 A1 | 12/2011 | Maguire et al. | |
| 2012/0022407 A1 | 1/2012 | Lechner | |

(Continued)

FOREIGN PATENT DOCUMENTS

WO    03/000146    1/2003

OTHER PUBLICATIONS

International Search Report & Written Opinion issued in International Application No. PCT/US13/45142 on Sep. 10, 2013.

(Continued)

*Primary Examiner* — Emily Schmidt
(74) *Attorney, Agent, or Firm* — Stephen H. Eland; Dann, Dorfman, Herrell & Skillman

(57) ABSTRACT

A method and apparatus are provided for locating a target region which is situated in a body of a subject, for example for the delivery of drugs. The system cooperates with a reservoir for receiving an injection fluid, a needle in fluid communication with the reservoir, and a sensor operable to detect a characteristic indicative of the fluid pressure in the needle. A signal generator supplies a success signal to an operator that indicates when the needle is present in the target region. A central controller controls the signal generator in response to signals received from the sensor.

29 Claims, 5 Drawing Sheets

(56) References Cited

U.S. PATENT DOCUMENTS

2012/0101410 A1     4/2012   Lechner
2014/0012226 A1     1/2014   Hochman

OTHER PUBLICATIONS

Ghelber et al., "Identification of Epidural Space Using Pressure Measurement . . . ", Regional Anesthesia and Pain Medicine, vol. 33, No. 4, Jul.-Aug. 2008, pp. 346-352.

Iff et al., "The Use of an Acoustic Device to Identify the Epidural Space in Cattle", The Veterinary Journal, 187 (2011) pp. 267-268.

Iff et al., "The Use of an Acoustic Device to Identify the Extradural Space in Standing Horses", Veterinary Anesthesia and Analgesia, 37 (2010) pp. 57-62.

Lechner et al., "Clinical Results with a New Acoustic Device to Identify the Epidural Space", Anesthesia, 57 (2002) pp. 768-772.

Lechner et al., "Clinical Results with the Acoustic Puncture Assist Device, a New Acoustic Device to Identify the Epidural Space", Anesthesia Analgesia, (2003) pp. 1183-1187.

Lechner et al., "Thoracic Epidural Puncture Guided By an Acoustic Signal: Clinical Results", European Journal of Anesthesiology, 21 (2004), pp. 694-699.

Lechner et al., "The Use of a Sounded-Enabled Device to Measure Pressure During Insertion of an Epidural Catheter in Women in Labour", Anesthesia, 66 (2011) pp. 568-573.

Tsui et al., "Reduced Injection Pressures Using a Compressed Air Injection . . . ", Regional Anesthesia and Pain Medicine, vol. 33, No. 2, Mar.-Apr. 2008, pp. 168-173.

Official Action issued in U.S. Appl. No. 11/208,400 on May 29, 2008, 10 pages.

International Preliminary Report on Patentability issued in International Application No. PCT/US13/45142 on Jan. 15, 2015.

International Preliminary Report on Patentability issued in International Application No. PCT/US06/29091 on Feb. 28, 2008.

DEVICE AND METHOD FOR IDENTIFICATION OF A TARGET REGION

TECHNICAL FIELD

The present invention relates generally to methods and apparatus for use in locating a target region which is situated in a body of a subject, for example for the delivery of drugs.

BACKGROUND ART

Locating a target region in a body, for example an anatomical cavity in a body of a patient, is important, inter alia, for anaesthetics, or biopsy or aspiration of material from the cavity.

For example, a regional anesthesia block of the epidural tissue-space is understood to produce effective transient anesthesia of the lower extremities of the body. It can be effectively used for a vast number of invasive procedures of the body, including but not limited to, child birth, prosthetic hip replacement, and a variety of other surgical procedures where anesthesia below the waist is required. It can also be effectively used for treatment of chronic and acute pain including, for example, "back-pain," ailments of the vertebrae and, compression of the accessory nerves of the spinal column. To achieve effective regional anesthesia and to block nerve transmission to the Central Nervous System an adequate volume of a local anesthetic solution must be deposited in close proximity to the spinal cord at a particular level of the vertebral column within the anatomic site known as the epidural "space."

The epidural space is that part of the vertebral canal not occupied by the dura mater and its contents. It lies between the dura and the periosteum lining the inside of the vertebral canal. It extends from the foramen magnum to the sacral hiatus. The anterior and posterior nerve roots in their dural membrane pass across the epidural space to unite in the intervertebral bodies, and the intravertebral discs. Laterally, the epidural space is bordered by the periosteum of the vertebral pedicles, and the intervertebral foramina. Posteriorly, the bordering structures are the periosteum of the anterior surface of the laminae, the articular processes and their connecting ligaments, the periosteum of the root of the spines, and the interlaminar spaces filled by the ligamentum flavum. The space contains venous plexuses and fatty tissue which is continuous with the fat in the paravertebral space.

The epidural fluid filled space (posterior epidural space) is a limited anatomic area with an irregular shape measuring in several square millimeters with respect to the cross section of the vertebrae and spinal column. The fluid filled space is very narrow and is associated closely with the dura of the spinal column with the ligamentum flavum closely adjacent. The fluid filled space therefore has to be clearly identified when the bevel or point of the needle exits the ligamentum flavum, as the dura will be punctured if the needle continues to penetrate. The standard technique for locating the epidural fluid filled space employs the "loss-of-resistance" (LOR) technique. This technique utilizes a low-friction syringe made of plastic or glass connected to an epidural Touhy needle (16 to 18 gauge). In addition, other pump driven systems have been developed to identify the epidural space by utilizing pressure monitoring with visual and acoustical representation of the fluid pressure within the system or at the tip of the needle.

When performed, the technique has the patient either in the sitting or lateral decubitus position. The patient should be encouraged to adapt a curled up position, as this tends to open the spaces between the spinous processes and facilitates the identification of the intervertebral spaces. Epidural injections can be sited at any level along the lumbar and thoracic spine, enabling its use in procedures ranging from thoracic surgery to lower limb procedures. Patients may also be placed lying face-down to expose the dorsum of the back when performing this procedure in conjunction with fluoroscopy.

The clinician palpates the vertebral column at the appropriate level of the vertebral column between vertebrae. Local anaesthesia is placed within the superficial tissues rendering the tissues of the area to be locally anesthetized. The dermis is then punctured using the Touhy needle and the needle is advanced while the clinician simultaneously applies pressure on the plunger of the syringe.

Insertion of the epidural needle continues and advances through the supraspinous ligament, with the needle pointing in a slightly cephalad direction. The needle is advanced into the interspinous ligament, which is encountered at a depth of 2-3 cm, until the subjective sensation of increased resistance is felt as the needle passes into the ligamentum flavum.

When using a LOR syringe the needle is advanced until the subjective "feel" of resistance by the clinician results in a distinct "back-pressure" on the plunger. The clinician must subjectively differentiate the "back-pressure" or resistance encountered to identify the location of the anatomic structure of the ligamentum flavum. The epidural fluid filled space is entered by the tip of the needle after it passes through the ligamentum flavum thus identifying a True-LOR During the advancement of the needle within the tissues it is common for the operator to identify a drop of pressure or a false-LOR. The false-LOR can be attributed to the needle tip entering into a low density tissue structure such as a vacuole (adipose tissue) or an anatomic structure with a high tissue compliance such as the interspinous tissues. Repositioning of the needle (forward and backward) occurs many times as a needle makes contact to bony vertebrae as one is attempting to find the correct trajectory to the epidural space. Any backward movement (retraction) of the needle along a path during the repositioning creates a drop in pressure in the fluid, which can result in a false-LOR further complicating the detection of a true-LOR.

The movement of the Touhy needle from penetration of the dermis to identification of the ligamentum flavum can vary from greatly in depth depending on the patient's physical size. The needle must travel along a distance through the tissues. Needle movements can create a False-LOR as previously described and this is magnified in those patients that are larger in size. Overweight patients also present a greater challenge, and with the morbidly obese patient the epidural injection may not be suitable because of the limitations of subjective nature of this technique. The morbidly obese patient has increased adipose tissue distributed throughout the body and those patients with increased adipose content present a greater challenge because of the distribution of vacuoles within these various tissue planes. Age appears to be an additional complicating factor because of the challenge presented by the reduced size of the anatomy of the epidural tissue-space and stenosis of the vertebrae such that needle tip contact to the bony surface often requires re-alignment and retraction of the needle to find the correct trajectory. Also, in small children tissue compliance is difficult to discriminate and False-LOR's are found making the procedure more dangerous.

False-LORs can lead to many problems. For example, excess fluids can be indiscriminately injected while trying to determine the location of the epidural space. The additional fluid released into these tissues can further complicate the identification of epidural space. Additionally, if the doctor has difficulty discriminating between a False-LOR and a True-LOR, the Touhy needle may be moved beyond the boundary of the epidural space and inadvertently advanced into and through the dura of the spinal cord producing what is termed a "wet-tap", which can have a dangerous long-term consequences to the patient.

Therefore, discriminating between a False-LOR and True-LOR for the practitioner is important when performing an epidural injection as this technique carries the risk of direct spinal cord injury resulting in transient or permanent nerve damage and even unintended death to the patient.

Ucha Calvo EPO 0538259A1 describes a method and apparatus for locating anatomical cavities such as the epidural space. The identification of the epidural space is based on a loss of resistance with a syringe by the emission of acoustic and visual warning signals which quantify and corroborate the tactile feelings of the operator. The method is independent of the pressure characteristics of the space to be detected. Ucha describes a first warning signal with pre-determined frequency and amplitude, which stops if the pressure returns to a constant recovery to the present value when the plunger is manually depressed, and a second warning signal with a different warning from the previous one used in both frequency and amplitude, in response to a drop in pressure in which the pressure cannot be recovered through manually depressing the plunger.

Thus Ucha describes two conditions, both initially represented by a sudden drop of pressure (i.e., a loss-of-resistance), which are then differentiated by one state in which a pressure can revert back to a pre-established level and a second state in which pressure cannot revert back to the pre-established pressure value. This system has the drawback that the differentiation between false-LOR and true-LOR is dependent upon the pressure placed upon the plunger by the user, and is thus subject to operator bias.

U.S. Pat. No. 6,200,289 (also published as WO/1999/52575) to Hochman et al. (incorporated herein by reference) discloses an automatic injection device that includes a drive mechanism that causes a therapeutic fluid to flow from a cartridge supported by a cartridge holder, a tube and a handle with an injection needle. The drive mechanism is connected to an electric motor and a sensor positioned at the motor output that measures the force applied by the motor to the drive mechanism. This force is then used to determine an internal characteristic such as a force or internal pressure generated during the injection process. This characteristic is then used as a control parameter by a microprocessor or controller which generates corresponding commands to the drive mechanism. In a particularly advantageous embodiment, the characteristic is used to calculate an exit pressure at which fluid is ejected by the device through an elongated tube. The electric motor is then operated in such a manner that the exit pressure is maintained at a predetermined level to insure that a patient does not suffer pain and/or tissue damage. Additionally WO/1999/52575 teaches the use of visual and constant current aural information, for example to feedback information about system pressures to the user. Although such information can assist clinicians in performing epidural injections, the problem of false LOR is not specifically addressed.

U.S. Pat. No. 7,922,689 (also published as WO/2003/000146) to Lechner discloses a device for locating an anatomic cavity that relies on an acoustic sound signal that is continuously representative of the pressure prevailing in the fluid (i.e. audible or visual warning signal). However this system has no capacity to discriminate between a drop in pressure related to a false-LOR versus a true-LOR, as this system only provides continuous acoustic feedback that does not distinguish between these two conditions.

Published U.S. patent application US2006/0122555 (also published as WO/2007/024399) to Hochman, describes an automatic injection device which includes a drive mechanism and a sensor used to determine an internal characteristic such as a force or internal pressure generated during an injection process. The entire disclosure of both U.S. Published Application No. 2006/0122555 and PCT Publication No. WO/2007/024399 are incorporated herein by reference. The internal characteristic is then used as a control parameter by a microprocessor or controller to determine the exit pressure of the fluid expelled by the device. This exit pressure is then used to identify the kind of tissue in which the injection is being introduced. This publication discusses how false-LOR can be identified when using the computer controlled drug delivery system with exit pressure control. Once the needle enters such a space the pump is turned on thereby quickly filling the space (or pressurizing the less dense tissue with fluid) such that the recorded exit pressure would once rise and objectively indicate a false-LOR.

Published patent application US2014/0012226 (also published as WO/2014/007949) to Hochman, the entire disclosure of which is incorporated herein by reference, describes an automatic injection apparatus which uses non-continuous fluid-flow of drugs to identify an intended injection site and includes a drive mechanism, a sensor and a controller for establishing fluid flow and pressure and preventing fluid flow until the pressure drops below a predetermined threshold. The pressure threshold is determined based on an internal pressure generated during an injection and more fluid will not flow until it drops below a predetermined pressure. An injection is performed to establish an initial pressure threshold and then to stop the fluid flow into a patient until the pressure drops below a predetermined pressure which allows fluid flow to resume, thus identifying a fluid filled tissue space. The initial pressure threshold is used as a control parameter for a microprocessor which controls the rate of injection. Fluid flows below certain pressures are also used to identify a specific location within the body during injections. Again false-LOR is identified by filling the space (or pressurizing the less dense tissue with fluid) such that the recorded exit pressure would once rise and objectively indicate a false-LOR.

U.S. Pat. No. 8,608,665 to Vad describes a device for pressure detection which may be used in conjunction with a syringe and needle. The device is described as including a pressure transducer, a microprocessor and a light emitting diode. The pressure transducer is configured to measure a first pressure at a first time and a second pressure at a second time. The microprocessor is configured to receive the first pressure and the second pressure from the pressure transducer, determine a pressure difference between the first pressure and the second pressure, and determine a time difference between the first time and the second time. Successful situation of needle is determined from the pressure difference and the time difference, which may be converted into a pressure-time 'slope'. A further (third) pressure at a later time point may also be measured to confirm success.

Published patent application US 2011/0301500 to Maguire et al. discloses an automated vessel puncture device using three-dimensional near infrared imaging and a robotically driven needle to providing simultaneous real-time diagnostic assays. It teaches that venipuncture is the process of obtaining a sample of venous blood for purposes of performing various tests. Samples are obtained manually from a vein or organ that is close to the surface of the skin by trained personnel, but there are problems inherent with these processes. This reference uses infrared imaging and a robotically driven needle to address the problem but does not use fluid pressure values to help indication the presence of vein or organ. Although pressure is mentioned, this refers to mechanical pressure resisting the movement of the mechanically driven needle to avert injury to the patient, not to fluid pressure in the needle.

It can be seen from the above that a novel system for guiding a needle to an anatomical target region which assists practitioners in discriminating between False-LOR and True-LOR would provide a contribution to the art.

SUMMARY OF THE INVENTION

The present invention provides, inter alia, a method and apparatus or device that enables practitioners to more easily perform the identification of anatomical target regions such as the epidural space.

The apparatus and related aspects disclosed herein are supported by data from a large scale study that utilized a device capable of measuring, monitoring and recording real-time pressure measurements when detecting the epidural space. This clinical research supports a new, more objective, approach to discriminating between False-LOR and True-LOR when identifying target regions.

Furthermore, clinical investigation into the operation of an apparatus devised to assist practitioners in performing such anatomical investigations has demonstrated that ergonomic devices which minimize the need for operator interpretation of subjective findings, or of complex feedback systems, or the need for additional locating actions, are advantageous.

The present invention provides a novel system for guiding a needle to an anatomical target region. The system provides a software logic and apparatus that can simplify discrimination between a False-LOR and True-LOR when performing these operations, such as detection of the epidural space, thereby improving the reliability and safety of such injections.

Thus in one aspect there is provided an apparatus for locating a target region which is situated in a body of a subject, the apparatus comprising:
a. a reservoir, or means for receiving a reservoir, for holding an injection fluid, which reservoir can be connected to a needle to be inserted into the body of the subject
b. pumping means, or means for receiving pumping means, capable of pumping said injection fluid from said reservoir into the subject at a flow rate,
c. feedback means comprising an audible signal generator for supplying an audible success signal to a user of the device that indicates when the needle is present in the target region,
d. a controller:
  i. capable of driving said feedback means; and
  ii. capable of receiving a real time pressure signal corresponding to the exit pressure of the injection fluid from the needle; and
  iii. comprising a computer including a memory for storing:
    (1) a first pre-determined pressure (P1) that is characteristic of a barrier tissue which must be encountered by the needle prior to arriving at the target region;
    (2) a second pre-determined pressure (P2) that is characteristic of the target region, wherein P2 is lower than P1 and wherein the computer is programmed to drive the feedback means to provide the audible success signal when the exit pressure drops below P2;
but wherein the computer is programmed such as to only to provide the audible success signal after the exit pressure has first exceeded P1.

The programmed logic, which can be implemented as software or firmware, is based upon two predetermined pressure limits that are identified in which the first predetermined pressure limit (P1, for example representative of the ligamentum flavum) is first identified and then to be followed by a second predetermined pressure limit (P2, for example representative of the epidural space). It should be appreciated that the invention requires a comparison of the measured pressure with absolute thresholds in a specific order, and is not based only on the magnitude of the change in pressure, or the rate of that change.

In operation, for example in the epidural injection, the logic is designed so that any sudden drop of pressure, i.e., a LOR, that occurs prior to the detection of the first predetermined pressure limit (P1) is disregarded and interpreted as a false-LOR. The requirement of the logic is that the first predetermined pressure value representative of the ligamentum flavum is first identified and is then to be followed by a drop of pressure to a second predetermined pressure value representative of the epidural space, which will elicit a 'success' warning or indication that the epidural space has been detected, i.e., that a true-LOR has occurred.

According to another aspect, the present invention also provides a method for locating a target region which is situated in a body of a subject, wherein the locating is done via a needle in fluid communication with a reservoir of injection fluid, the method comprising use of an apparatus of the invention.

For example a method is provided for locating a target region which is situated in a body of a subject with a needle in fluid communication with a reservoir, while reducing the likelihood of misidentifying the region through a false loss of resistance, the method comprising:
(i) providing a reservoir containing injection fluid, tubing in communication at one end with the reservoir and connected at the other end to a needle to be inserted into the body of the subject;
(ii) providing a sensor arranged to determine a resistance measurement of the injection fluid when injection fluid is pumped into the body of the subject through the needle at a flow rate;
(iii) providing a pressure calculation element configured to receive the resistance measurement from the sensor and calculate a real time pressure signal;
(iv) advancing the needle slowly into the patient while pumping the injection fluid into the patient;
(v) detecting the first predetermined pressure threshold (P1) characteristic of a barrier tissue which will be encountered by the needle prior to arriving at the target region
(vi) detecting the second predetermined pressure threshold (P2) which is characteristic of the target region; and
wherein the computer is programmed to drive the feedback element to provide the audible success signal when the exit pressure drops below P2;
but wherein the computer is programmed such as to only to provide the audible success signal after the exit pressure has first exceeded P1.

The method may also include the step of ceasing advancement of the needle in response to the step of detecting P2.

The invention also provides use of an apparatus as described herein for locating a target region which is situated in a body of a subject, said locating utilizing the needle in fluid communication with a reservoir, while reducing the likelihood of misidentifying the region through a false loss of resistance The invention described herein thus provides for improved safety and predictability when performing a procedure to identify the epidural space.

In some embodiments of the invention, the needle is a catheter needle.

In some embodiments of the invention, the injection fluid comprises a drug.

According to another aspect, the present invention utilizes a warning at both specific predetermined pressure values. The first (optional) warning is elicited when the pressure exceeds P1, while the second is the success warning once the pressure drops below P2.

Both an audible and/or visual signal information may be provided when the system identifies the first predetermined pressure threshold that is to be followed by a second predetermined pressure threshold.

In one embodiment the P1 and\or P2 warnings may take the form a verbal announcement of the pressure threshold value that has been selected.

In some embodiments the computer is programmed such as to only provide the audible success signal when the calculated pressure drops below P2 within 1, 2 or 3 seconds of dropping below P1.

The apparatus may use a computer programmed with software which sets a flag condition after the calculated pressure exceeds P1 to thereby permit the feedback element to provide the audible success signal when the calculated pressure drops below P2.

In some embodiments the computer is programmed such as to only to provide the audible success signal when the calculated pressure drops below P2 within 1, 2 or 3 seconds of dropping below P1.

Thus the apparatus may use a computer programmed with software which sets a flag condition after the calculated pressure exceeds P1 to thereby permit the feedback element to provide the audible success signal when the calculated pressure drops below P2 only if the drop occurs within 1, 2 or 3 seconds of dropping below P1.

The first predetermined pressure value (P1) is higher than the second predetermined pressure value (P2) in this example for the detection of a True-LOR. As an example this value may be set between 100 and 250 mm/Hg, for example 175 mm/Hg. Examples of P1 values appropriate to the target region in question are described in more detail below.

Once the first predetermined pressure value has been identified the software logic is enabled to detect the second predetermined pressure value that is set at a low pressure value, in this example the second pressure value is set to 50 mm/Hg. When a subsequent sudden drop of pressure now occurs the device will provide a second acoustic warning which is representative of the pressure dropping below the second predetermined pressure value. The acoustic warning provides an objective threshold at a predetermined pressure value that is representative of the pressure of the epidural space. Therefore, the logic of the software distinguishes between pressure drops that occur prior to the detection of the ligamentum flavum and those that occur after the detection of the ligamentum flavum. This enables one to distinguish between a False-LOR and the True-LOR.

In preferred embodiments the pumping element forms part of the drive unit. For example the pumping element may be one or more motors plus one or more syringe armatures.

In preferred embodiments the controller is capable of modulating the flow rate in response to the received real time pressure signal—for example it may modulate the flow rate to substantially zero when the pressure signal indicates the needle exit pressure is above P1. It may modulate the flow rate by reducing the flow rate to 50% when the pressure signal indicates the needle exit pressure is above 80% of P1.

In preferred embodiments the feedback element generates different sound types reflecting the operation of the pumping element, and the presence, absence or magnitude of the flow rate.

Typically, the reservoir is formed by one or more syringes which fit into a cavity or armatures to be operated by a motor in the drive unit.

The syringe, or each syringe, may form part of a "disposables" assembly, along with tubing, needle and a pressure transducer for generating a real time pressure signal corresponding to an instantaneous pressure at the point of the needle. The transducer may be connected in-line a between the opposite end of the syringe and the tubing.

In a preferred embodiment the drive unit has a housing with a syringe cavity for removably holding the body of a syringe in an axially fixed position on the housing, and a plunger recess wherein the plunger is free to move, the syringe armature having a stage movable along the plunger recess, the plunger having thumb pad and the stage having at least one pivotally mounted and spring-loaded hook for engaging the thumb pad when the stage is moved to engage the thumb pad to axially connect the stage to the thumb pad so that movement of the stage in opposite directions moves the plunger in opposite directions, the syringe armature including a sensor for sensing that the stage has been moved to engage the thumb pad, the computer being programed to stop the movement of the stage under the influence of the sensor when the stage has engaged the thumb pad.

It is also contemplated that the device may optionally contain an element for recording and/or displaying relevant injection data including, for example, instantaneous flow rates, pressures, and injection amounts. All measurements and information may be presented to the clinician in "realtime" so that the clinician may determine whether the injection is being delivered to the intended location and/or correct tissues and so that the clinician may modify the injection technique accordingly. In addition, the measurements may be recorded for later review and documentation of the clinical event.

It is also contemplated that multiple syringes driven by separate syringe plungers may be used to allow multiple drugs to be injected as well as a second syringe drive that does not require a pre-determined pressure to be reached. The second drive can be programmed on a specific flow-rate to allow infusion of a drug such as local anesthetic and/or other therapeutic drugs into a variety of tissues.

In yet another embodiment the device may contain two distinct syringe drives in which both are capable of modulation based on fluid-pressure as previously herein described.

In a further embodiment, a device for locating a target region which is situated in a body of a subject is provided. The device includes a reservoir for receiving an injection fluid, wherein the reservoir comprises a connector for connecting the reservoir with a needle to be inserted into the body of the subject. The device further includes a sensor for detecting a characteristic indicative of the fluid pressure in the needle. A signal generator supplies a success signal to a user of the device that indicates when the needle is present in the target region. The success signal may be acoustic, visual or tactile. The device also includes a fluid controller configured to control the flow of fluid from the reservoir and a central controller connected with the sensor for receiving signals from the sensor. The central controller is operable to control the signal generator in response to signals received from the sensor. Additionally, the central controller is operable to control the signal generator to provide the success signal in response to the presence of two conditions: (i) receipt of a signal from the sensor indicative of a first pressure threshold being exceeded; and (ii) receipt of a subsequent signal from the sensor indicative of the pressure falling below a second pressure threshold.

In yet a further embodiment an apparatus is provided for locating a target region which is a fluid-filled anatomic space situated in a body of a subject, wherein a barrier tissue is pierced to access the anatomic space. The apparatus is configured to cooperate with a reservoir for receiving an injection fluid, a needle in fluid communication with the reservoir, and a sensor operable to detect a characteristic indicative of the fluid pressure in the needle. The apparatus include a signal generator and a central controller. The signal generator supplies a success signal to an operator that indicates when the needle is present in the target region, wherein the success signal is acoustic, visual or tactile. The central controller is operable to control the signal generator in response to signals received from the sensor. The central controller is operable to control the signal generator to provide the success signal in response to the presence of two conditions: (i) receipt of a signal from the sensor indicative of a first pressure threshold being exceeded; and (ii) receipt of a subsequent signal from the sensor indicative of the pressure falling below a second pressure threshold.

These and other embodiments are described in more detail hereinafter.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DETAILED DESCRIPTION

Figure 1A:
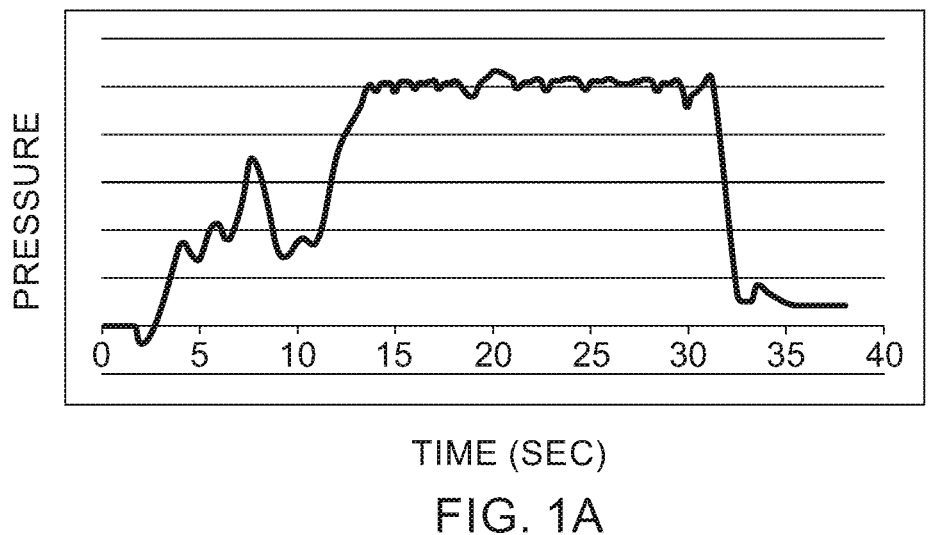
FIG. 1A is a graph illustrating real-time pressure measurements obtained for a first patient when performing detection of the epidural space.
Figure 1B:
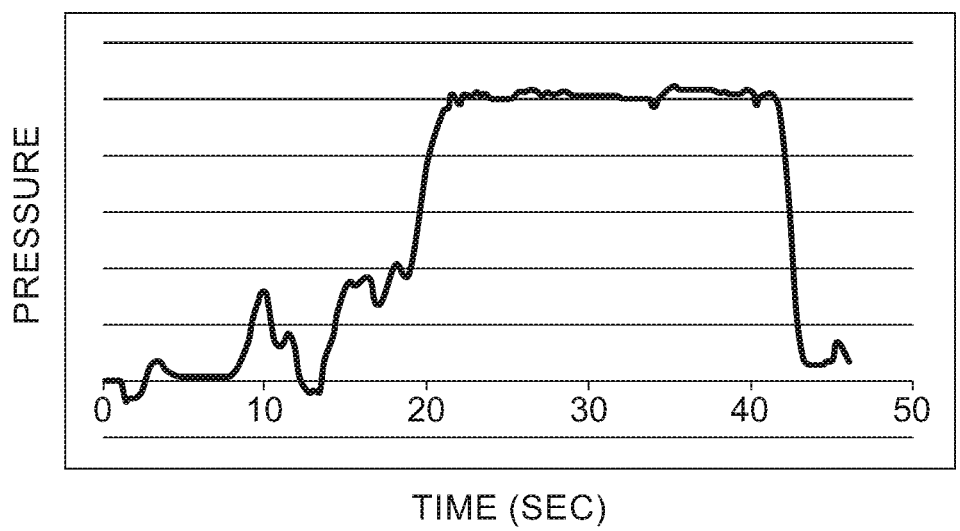
FIG. 1B is a graph illustrating real-time pressure measurements obtained for a second patient when performing detection of the epidural space.
Figure 1C:
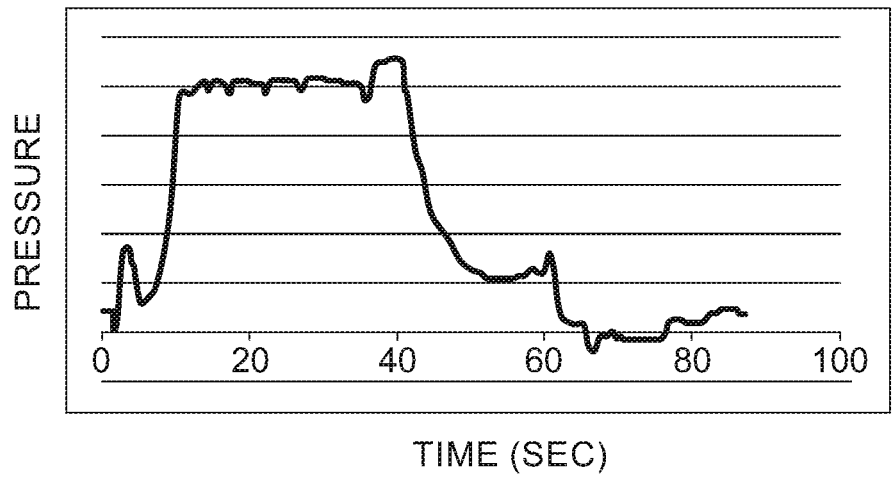
FIG. 1C is a graph illustrating real-time pressure measurements obtained for a third patient when performing detection of the epidural space.
Figure 1D:
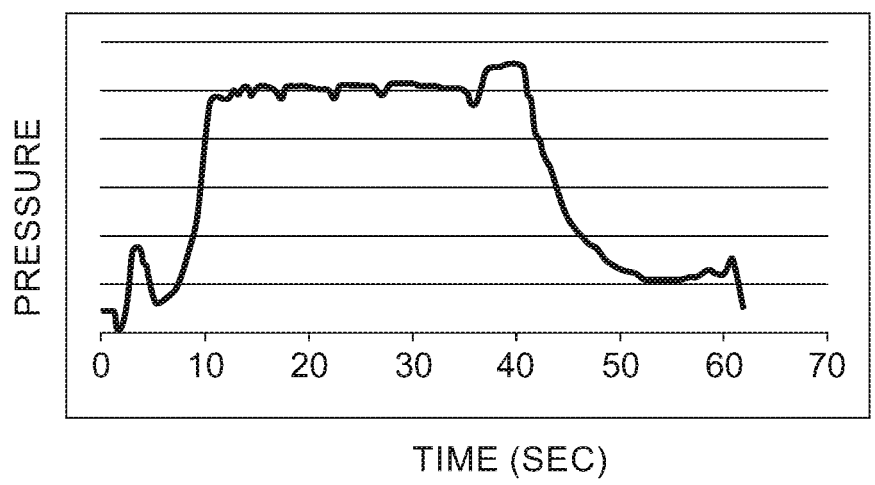
FIG. 1D is a graph illustrating real-time pressure measurements obtained for a fourth patient when performing detection of the epidural space.

A method and device are provided for identifying anatomical target regions, such as the epidural space, which reduces the detection of false-positive loss-of-resistance (false-LOR or false-positive-LOR) in non-specific tissues of the body. The device is designed with hardware and a software logic that detects a false-positive-LOR and enables detection of a true-Loss-of-Resistance with a high level of specificity and certainty.

In preferred embodiments a non-continuous alert signal and mechanic logic is provided to indicate a specific high pressure threshold warning to be followed by a specific minimum pressure threshold based on a software logic interpretation which helps avoid the commonly detected false-LOR prior to the detection of a true-LOR.

In one embodiment the apparatus of the invention includes a software logic capable of incorporating a first pre-determined pressure value representative of the ligamentum flavum in which said first pre-determined pressure value is required to be reached prior to the detection of a second pre-determined pressure value representative of the epidural space. Encountering the first then second pre-determined pressure values will elicit a warning signal related to a specific objective value also referred to as a "success signal" herein.

In yet another embodiment the apparatus of the invention includes a software logic incorporating a first pre-determined pressure value representative of the ligamentum flavum to be followed by a second condition within the software logic that is capable of detecting the slope of the decrease (i.e., a sharp and sudden drop) in pressure prior to a detection of the second pre-determined pressure value representative of the epidural space. Encountering these first, second and third conditions within the software logic will elicit an audible warning signal related to a specific objective value also referred to as a "success signal" herein.

In the preferred embodiment, an exemplary value for the first pre-determined pressure value is 175 mm/Hg. An exemplary value for the second pre-determined pressure value is 50 mm/Hg.

The system, therefore, provides a software logic that enable one to eliminate the detection of a false-positive LOR prior to reaching a pre-determined pressure threshold that is representative of the ligamentum flavum. In addition, the system objectively identifies the true-LOR after a high pressure threshold had been identified.

Once the true-LOR is detected from a rapid and sudden drop from the pre-set high pressure, the pressure drops below the second pre-set low pressure threshold value representative of the epidural fluid filled space. After passing the first and second pressure thresholds, the needle is immobilized during a 3 to 5 second observation period. If the pressure should raise from below this second pre-set low pressure threshold value it may have occurred from over advancing the needle such that contact is made to the dura membrane. In such case, it is advisable to retract the needle and restart the process to ensure that the pressure remains below the second pre-set low pressure threshold to ensure that the needle has remained in the epidural space. This adds an additional level of safety and predictability to this technique.

The method and apparatus thus provide a reliable and reproducible system for administering an injection to a patient in a desired fluid-filled tissue location which previously required years of training and formerly possessed a high degree of subjectivity, and, as a result, was open to misinterpretation and human error. The present technology provides a more efficient and ergonomic system to detect the True-LOR thereby saving time, money and improving patient safety. It enables more confidence and a more rapid learning curve for those doctors that need to perform this vitally important procedure. It reduces medical costs by reducing the time needed to become proficient in performing such a technique-sensitive procedure while simultaneously providing improved safety and predictability.

As explained above, the present system employs an objective approach that is supported by clinical data. Over 200 procedures were reviewed in which a pressure sensing device was compared to the standard technique for identifying the epidural space. One hundred patients served as the control (i.e., standard technique of LOR using an LOR Syringe) and another 100 patients were treated using a pressure sensing device that controlled exit-pressure and stored exit-pressure in real-time data files. Fifty patents were treated for lower back-pain for which the presence of the needle in the epidural spacing was confirmed using fluoroscopy. Fifty more patients were treated for labor and delivery with success confirmed by documented effective regional anesthesia achieved.

FIGS. 1A-1D show 4 representative graphs from a large scale (more than 200 interventions) clinical study of real-time pressure measurements obtained when performing detection of the epidural space data set. Although the profiles differ, it can be seen that a false-positive LOR occurs prior to reaching the maximum pressure value in each example, and the epidural space is encountered immediately after this maximum pressure was experienced.

The data from the clinical study illustrate several conclusions, including:
(1) A maximum pressure representative of the ligamentum flavum was consistently identified prior to the epidural space, which was typically preceded by a sudden and sharp drop in pressure which represented the transition from ligamentum flavum to the entrance into the epidural space. From this data set it became apparent that a high pressure threshold is achieved prior to a sharp and sudden drop of pressure.
(2) Numerous cases demonstrated an initial sharp and sudden drop in pressure which occurred prior to reaching the high pressure threshold. All of these cases were identified as a False-LOR. The drop in pressure was attributed to either minor retraction of the needle because of redirection, premature contact to bone, or the position of the needle tip within a vacuole of adipose tissue. The actual cause for this drop in pressure could not be conclusively identified in this study. Nevertheless this must be interpreted such that any drop in pressure which occurs prior to reaching the high pressure value representative of the ligamentum flavum is indicative of a False-LOR. This was confirmed in each case as the pressure went on to reach the pre-determined high pressure threshold, after which a sharp and sudden drop in pressure occurred.

After this sharp and sudden drop in pressure, the pressure value dropped below a lower pressure value. In this study, the lower pressure value was 50 mm/Hg and the pressure value stayed below this value for an observational period between 3 seconds to 5 seconds. During the study, once the sharp and sudden pressure drop occurred the needle was instantly immobilized. In other words, no further needle movements occurred after the sudden pressure drop.

The pressure identified for the ligamentum flavum produces values ranging from 175 mm/Hg to as high as 500 mm/Hg or higher. The connective tissues of the body produce pressures between 75 mm/Hg and 125 mm/Hg when injected with fluid at a rate of 0.07 mL/sec, while the epidural space produces pressure values between 0 mm/Hg to 50 mm/Hg when a fluid is injected into this fluid filled cavity at a rate of 0.05 mL/sec.

While the exact flow rate per se is not a critical feature of the invention, those skilled in the art will be able to select a flow rate high enough to provide sufficient responsiveness to the user in terms of the pressure measurement and the rate at which the needle is advanced, while not so excessive so as to introduce unnecessary volumes of injection fluid into the subject, or risk missing the true-LOR by pressurizing the target region too quickly.

Generally a flow-rate of between 0.005 cc/sec to 0.20 cc/sec will be appropriate for the subject and intervention, though 0.01 to 0.15 cc/sec may be preferred.

More specifically, a flow-rate range will be adopted that is capable of providing a responsiveness to a change in pressure that can be detected rapidly. Using a flow-rate that is too slow will produce an outcome in which the detection of a false-positive LOR is unnecessarily delayed. As has been described above, a false-positive LOR typically occurs when a compartment such as a fat vacuole is entered into prior to reaching the high pressure value. This compartment will produce a sharp and rapid drop in pressure. When using an appropriate flow-rate within the range identified, the compartment will fill rapidly and the pressure will continue to move to the high pressure threshold value (P1) so that the user continues to advance the needle within the tissues. If the flow-rate is set too low, the procedure will increase in time and the response of the pressure change will not be detected within a clinically acceptable time frame, typically within 3 to 5 seconds.

Nevertheless, if the flow-rate selected is too rapid, when the system detects a true-LOR identifying the epidural space there is a risk that an excessive amount of fluid will be introduced into the space. In addition, due to the volume limits of the epidural space, an excessively rapid flow-rate could cause the epidural space to fill with excessive fluid leading the pressure to raise again within a short time frame even when a true-LOR has been identified.

As explained in more detail below, the apparatus of the present invention will preferably allow for adjustment of the flow rate during the procedure, either automatically based on the pressure, or manually by the user.

It should be noted that some previous research measuring the pressure within the epidural space was conducted using monometers that measure pressure in a static condition in which fluid is not being used to (indirectly) measure the pressure within the space. Pressure measurements based on resistance measurements of an injection fluid pumped into the body of the subject through a needle (as in the present invention) are to be expected to be higher than static measurements.

In the present system the relevant tissues have their own pressure density characteristics which are represented as measurable pressures that can be elicited within a given tissue type. It is analogous to the concept of the compliance of a particular tissue. The density or resistance of the tissue is measured using the pressure of a fluid infused into the subject from the system, which is capable of detecting pressure resistance during infusion.

Preferred values for the P1 threshold representing ligamentum flavum are e.g. above a pressure of threshold selected from 100 to 500 mm/Hg and are preferentially above 125 mm/Hg.

Preferred values for the P2 threshold representing the epidural space (fluid filled cavity) are e.g. below a pressure of threshold selected from 20 to 75 mm/Hg and are preferentially below 50 mm/Hg.

Thus the present system pertains to determining the location of and optionally delivering drugs in fluid-filled tissues such as the epidural space.

Nevertheless, in the light of the present disclosure it will be appreciated that the invention can be applied mutatis mutandis to other target regions. The invention has particular utility for the injection of drugs, such as, but not limited to, local anesthetic solutions, cortico-steroids, and other drugs typically injected into a fluid-filled tissue space for therapeutic purposes.

The present system provides a method and device that enables the practitioner to accurately identify fluid-filled tissue space while minimizing the risk of misidentification arising from false-LOR, and can be used to limit the placement of drugs into non-targeted tissues. The method may be performed for either a diagnostic, or a therapeutic procedure, or both.

The current device utilizes the pressure of a fluid from a needle or catheter ("the injector") following placement of the needle/catheter within the tissue in order to properly identify the accuracy of placement and to monitor the (correct) placement during an injection or aspiration.

In one embodiment, the devices and methods of this invention are used to administer an epidural injection.

It another embodiment the device may be used for aspiration of a fluid-filled tissue space after the identification of a fluid-filled space is determined. Aspiration may be used either to withdraw a sample of tissue or extracellular fluid, or may be used to determine the correct placement of the injection needle. During an aspiration procedure, the "entry pressure" is measured in the same manner as the pressure within the fluid-filled tissue space, which is characterized by a loss of pressure. Likewise, false loss of pressure is also identified during an aspiration procedure because the internal tissue structure (i.e., cyst) will be quickly drained of its contents and the entry pressure will rise above the threshold entry pressure.

Frequently, procedures that require an epidural injection of anesthetic are lengthy and, in addition to the initial (loading) dose, one or more subsequent (maintenance) doses are required. Typically, an indwelling catheter is used to administer the plurality of doses. In another embodiment, the system provides a method for administering an epidural injection requiring a plurality of injections wherein, during administration of the second (and subsequent) doses, the pressure of the fluid at an interface between the end of the injector and the tissue of said patient is calculated, and the flow rate of the injection fluid during said second injection is controlled such that the pressure does not exceed the pre-set high pressure. Likewise, this technique may be used for indwelling catheter maintenance (i.e., to determine whether the catheter remains in a target tissue such as the epidural tissue space) whether or not an additional injection is contemplated or desired at that time.

The present system utilizes a pumping mechanism to pump injection fluid into the subject. The pump may be combined with the drive unit prior to use, but will preferably be integral with the drive unit. The pump will generally comprise a motor and a coupling element for driving fluid from the reservoir—for example a syringe armature. Infusion pump devices and systems are well known in the medical arts, for use in delivery or dispensing a prescribed medication to a patient.

The motor, the coupling associated with the motor, and the electronic controller discussed below may be at least partially disposed within the apparatus housing for protection.

In one embodiment the device of the system has two distinct drives to allow the placement of multiple syringes onto a single device. In such embodiment a first drive is used with a separate syringe, tubing set and needle for the delivery of a first drug and a second drive contains a separate syringe, pressure transducer, tubing set and needle for a second drug. Each drive is capable of the features described herein. In addition, one of the two drives may also be used without the capacity to sense pressure and be entirely used to deliver a drug at a specific flow-rate. This drive may be used to deliver a local anesthetic prior to the use of the second drive in which a first and second pre-determining pressure limiting feature is used to identify a fluid-filled tissue space. This permits the superficial soft-tissue anesthesia prior to attempting to identify the target region.

In embodiments of the system, the injection fluid may contain, for example, an anesthetic and the needle is adapted for insertion into the epidural fluid-filled tissue space. It is contemplated that either the pharmaceutical-containing or a pharmaceutical-free (testing) fluid is used to identify the fluid-filled tissue space during the needle placement phase of the procedure. A pharmaceutical-containing fluid, such as local anesthetic, corticosteroid, combined anesthetic-corticosteroid or other active pharmaceutical agents could be used to identify the target. Suitable pharmaceutical-free fluids include, for example, physiological saline, phosphate-buffered saline, artificial cerebral spinal fluid, Ringers, 5% dextrose, or filtered air. Once the fluid-filled tissue space is identified using the pressure difference method, the injection fluid is changed (i.e., requiring a plurality of fluid reservoirs) to a pharmaceutical-containing fluid. The use of a pharmaceutical-free fluid during the needle placement phase minimizes or eliminates the delivery of the pharmaceutical to non-target tissues.

In the present system the sensor may be an in-line sensor placed between the pumping mechanism and the needle, but is preferably between the pumping mechanism or syringe and the beginning of the tubing set which measures the pressure of the injection fluid. Alternatively, the sensor may be within a thumb-pad that will make physical contact to the syringe plunger.

Preferably, a sensor, such as a transducer, is used to sense the force or pressure generated by the motor and applied by the plunger within the fluid storage device. The transducer may measure the force between the syringe adapter and/or the remaining housing of the device.

The transducer may include a size sensing device that senses a change in dimension of an element of the device, said change being indicative of the force or pressure of the drug within the system and the pressure. For example, the change in size of the tubing may be used as an indicia of this force or pressure. In another embodiment, the pressure within the tube is measured externally and used to determine the fluid pressure.

The pressure resistance measurement is optionally converted into a visual signal and displayed in real-time on a feedback display, such as a screen. The screen display graphs of the pressure values and enable a data marker to be added to the data set by touching the screen. This data point will set a numeric value onto the screen as well as into the data set. This enables the user to record annotated information after the procedure is concluded based on the marker number. In addition audible acoustic sound is provided to the operator. This acoustic sound provides signals to the operator indicating warning pressure thresholds and operational information such as motor function and hence the presence or absence of a fluid flow rate The measurements presented to the doctor on screen so that the doctor can determine or confirm whether the injection is being delivered to the correct tissues and proper pressure values are being recorded, this cannot be ascertained from the acoustic information provided. In one embodiment, a horizontal line is shown on the visual display to represent the predetermined P1 and P2 value currently active during graphing of the data. In addition, the pressure measurements, fluid volume, time and input markers are also recorded for later review and documentation of the clinical event. The first pre-determined high pressure limit threshold, second pre-determined low pressure limit threshold value as well as control of flow-rate can be pre-defined to ensure that excessive pressure and/or flow-rate are not used during this process.

The controller utilized in the present system includes an input mechanism that is generally capable of accepting user-inputted parameters including, for example, a first pre-determined high pressure value (P1), a second pre-determined low pressure value (P2). For example, the system may include a touch screen or one or more input buttons. The controlled includes a computer, and these values are stored in a memory of the controller.

The controller of the drive unit will also preferably be capable of modulating the flow rate, including reducing the flow rate to substantially zero. This is done by controlling the pump mechanism.

Thus the controller utilized in the present system may also be capable of accepting a user-inputted parameter which is a desired flow rate.

As explained in more detail below, the controller of the drive unit will also preferably be capable of modulating the flow rate in response to the received real time pressure signal.

Thus in one embodiment the system provides a device and method for identifying the epidural space by providing a fluid reservoir, an injection fluid, a pumping mechanism, wherein the reservoir can be connected to a needle for insertion into the patient; pumping the fluid from the reservoir into the patient; calculating the pressure of the fluid at an interface between the needle and the tissue of said patient, and controlling the flow rate of the injection fluid such that the pressure does not exceed a pre-set high pressure and then the flow rate resumes once the pressure drops below a pre-set pressure at which time once the pressure has descended below a second pre-set low pressure the device elicits an audible warning to indicate an objective pressure threshold has been crossed.

The flow rate may be controlled by the pressure signal in a binary manner. For example the flow rate may be reduced to zero (i.e. the motor or pumping mechanism stopped) when the pressure signal shows the needle exit pressure is above P1.

However, the flow rate may be controlled by the pressure signal in a more complex manor. For example, in one preferred embodiment if the pressure rises to exceed 80% of the pre-determined high pressure value (P1) the flow-rate is reduced by 50% of the rate. This ensures a more gradual reduction of the flow-rate as it approaches the pre-determined high pressure value setting P1.

When the pressure drops below the P1 value the motor starts again.

In other embodiments the function relating the automatic flow rate adjustment in response to the measured fluid pressure may be user-defined, for example in response to other threshold values.

It will be appreciated that even in embodiments where the controller is used to automatically adjust flow rate, the flow rate may be also be directly user adjusted, or over-ridden.

The flow-rates can be controlled by the user by depressing a foot control and pre-set to multiple specific speeds when used. However, in the preferred embodiment there is only one speed that is used. In another embodiment two speeds are provided and a user can change from Speed-1 to Speed-2 by depressing the foot pedal or activating a button on the screen to change the speed of the motor. The same is true when the instrument is set to have 3 speeds. Three specific distinct speeds are pre-set and activated an input device, such as a foot control, touch screen interface or buttons on the front of the device. The behavior of the instrument to each speed is the same.

As explained above, typical desired flow rates are in the range 0.005 cc/sec to 0.20 cc/sec, in yet another embodiment the flow rate may be between 0.003 cc/sec to 2.0 cc/sec.

Put another way, this embodiment of the present device utilizes a pre-determined first fluid pressure to prevent the flow of a drug within a non-targeted (first) tissue site and to resume a flow of fluid once the pressure either drops below a pre-determined same pressure, which is typically P1 herein.

The use of different flow rates (or indeed zero flow rate) can provide benefits to the procedure. For example it can be used to prevent flow of the drug at a specified value and then allow fluid-flow to resume once a pre-determined pressure value is below said value. This may be used during the maintenance phase of the procedure to ensure that the injector remains within the intended tissues such as the epidural space.

Some medical procedures may require an initial epidural injection (i.e., loading dose) followed by periodic maintenance doses in order to maintain the desired level of anesthesia. An indwelling catheter may be inserted into the epidural space and remain attached to the injection device throughout the procedure. The patient may be moved between the loading dose and one or more of the maintenance doses. Such movement may cause a correctly placed catheter to migrate from the epidural tissue space into a non-target tissue. In preferred embodiments the present device can monitor the pressure during all periodic doses (i.e., the loading dose and all subsequent maintenance doses). Thus, drug will not be injected into tissues that are unintended and non-therapeutic to the patient. Additionally, the clinician is alerted should the catheter migrate during the maintenance phase. The current device utilizes non-continuous fluid-flow and pre-determined pressures to properly identify the accurate placement of an indwelling catheter while limiting the flow of drug into non-targeted tissues.

Thus, the advantages of this embodiment of the present device over the prior art include identification of fluid filled tissue space such as the epidural space, while utilizing a negligible volume of drug-containing solution.

According to the principles of this disclosure, the pressure is measured using the pressure/force of a fluid injected/ infused from a computer-controlled drug delivery system capable of detecting pressure resistance during infusion. The pressure resistance measure is preferably converted into a visual as well as audible signal. The computer-controlled drug delivery system is continuously modulated based on the pressure generated producing a non-continuous fluid flow. Thus, the flow-rate is variable and is dependent on the pressure of the system. In this way, the pressure may be a primary controlling variable of the system.

The flow-rate, therefore, may become a secondary variable that is modulated within a pre-determined range in order to maintain the desired fluid-flow. In one specific embodiment, the fluid flow is stopped at pressures exceeding a pre-determined threshold (maximum permitted pressure). The flow-rate, as a secondary variable, may be limited so that fluid injections are not unduly rapid under low pressure conditions. It is contemplated that the relationship between pressure and fluid flow rate may either be binary or continuous. A binary relationship exists when the injection device is configured to deliver a fluid at a single, pre-determined flow rate for any pressure less than the pre-set maximum. Thus, the fluid flow is either on or off based on whether or not the pressure exceeds the threshold. Alternatively, the flow rate may be modulated as a function of pressure. In this case, flow rate will be reduced as the maximum pressure is approached and increased as the pressure drops. Optionally, the flow rate may be limited to a first pre-set maximum pressure and a flow rate resumes at a second distinct pre-determined pressure.

As explained above, in preferred embodiments two acoustic warning are employed corresponding respectively to the first and second pre-determined pressures (P1, P2). The acoustic sounds may consist of, but are not limited to, a spoken word, such as "Maximum Pressure", "High Pressure", "High Threshold", the announcement of the numeric value or a tone.

Audible feedback, such as characteristic tones, may also be provided elsewhere to inform the user that a particular flow rate is occurring. In one embodiment, the constant flow rate is represented by a repeating tone during fluid flow.

When the flow rate is computer controlled, a second audible signal, such as a tone, may be provided to the user when the high pressure threshold (P1) is reached. This is followed by a second signal which indicates that the motor is no longer operating. In another embodiment when the pressure drops below the second pre-determined pressure value (P2) from the high pressure value, the system may provide a third audible signal to the operator. This third signal may be an acoustic sound or it may be comprise a series of tones or it may be a spoken word, such as "Low Pressure", "Low Threshold", the announcement of the numeric value or a tone, to be followed by a third acoustic constant repeating tone elicited to denote that the pressure has descended below the second predetermined pressure value and the motor is functioning.

The system may include a disposables assembly made up of a syringe, pressure-transducer, tubing set and needle plus one of a variety of unique proprietary connection adaptors (disclosed herein is called an "ID-Connector" or abbreviated as "ID-Connector") to be affixed as part of the disposable assembly used in conjunction with a computer-controlled drug delivery system.

Figure 3A:
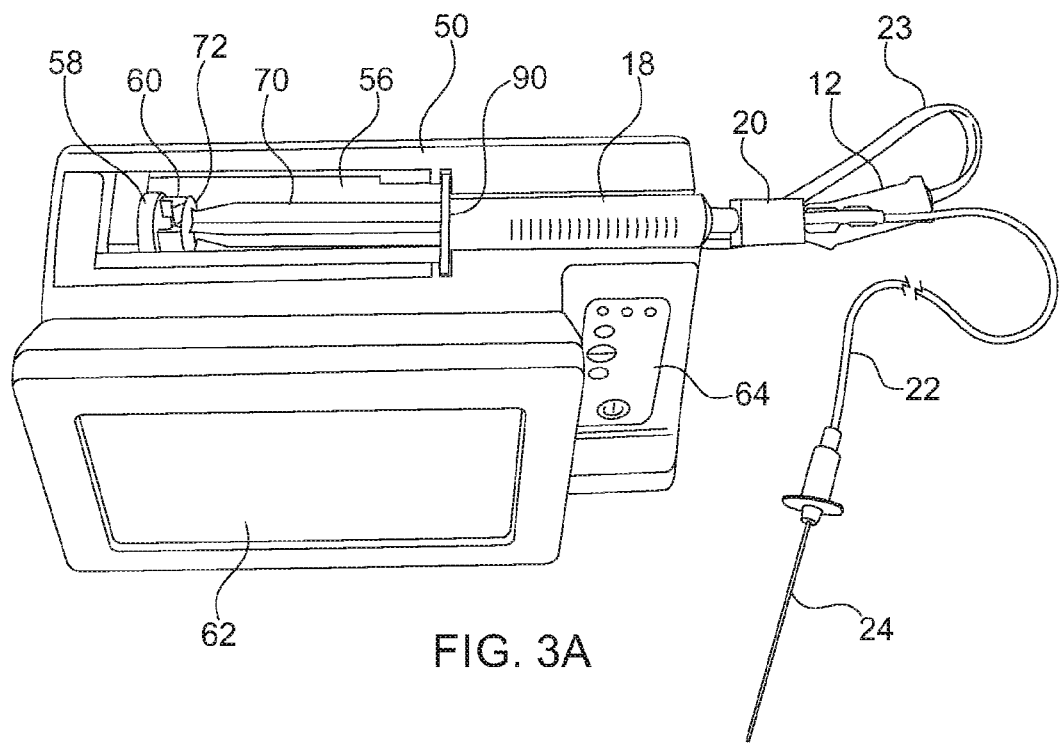
FIG. 3A is a top view of a computer-controlled drug delivery unit housing with a disposables assembly in place for use.

To ensure that the appropriate disposable components are used with the computer-controlled drug delivery system, a proprietary connector 12 in FIG. 3A may be included. The proprietary adaptor connection 12 ensures that only authorized, correctly configured, correctly sized and sterilized disposables assemblies are used with the instrument. This is accomplished in the structural implementations described in more detail in WO/2014/007949, the entire disclosure of which is hereby specifically incorporated herein by reference.

The connection 12, electronically connects the in-line, electronic pressure transducer 20 to the computer-controlled drug delivery instrument 50, using an external data cable 21 from transducer 20 to the first mating part, that is plugged to the second mating part, and is connected by a second cable 23 and the jack that is plugged into the instrument 50. The pressure-transducer 20 is connected inline, that is, immediately between the end of the cylinder of syringe 18, and one end of tubing 22, e.g. by Luer connections that have been permanently bonded as explained below, so that the instantaneous, actual fluid pressure in the drug delivery line is being sensed and used by the instrument, which provides a close approximation to the actual, instantaneous fluid pressure at the point or tip of the needle 24, and therefore, at the location in the patients body where the tip is located.

The electronic pressure-transducer or sensor 20 provides pressure data via the electronic data cable and connector 21-12-23, that is connected directly to the unit 50 to collect such pressure measurements. By incorporating the intervening proprietary connection 12 between the electronic pressure-transducer 20 and the computer-controlled drug delivery instrument 50, a verification and/or authorization checkpoint can be established. The proprietary connection 12 is used to identify and verify the connected components. The disposable components are provided as an authorized single-use, bonded disposable set in which all components are glued together as described in WO/2014/007949

The electronic pressure transducer 20 can, for example be any one of various piezoelectric pressure sensors available from Merit Medical Systems, Inc. such as the Meritrans® Pressure Transducer item MER212. As noted above, the proprietary connection 12, and other optional authorization schemes which may be used with the system, are described in WO/2014/007949.

Figure 3B:
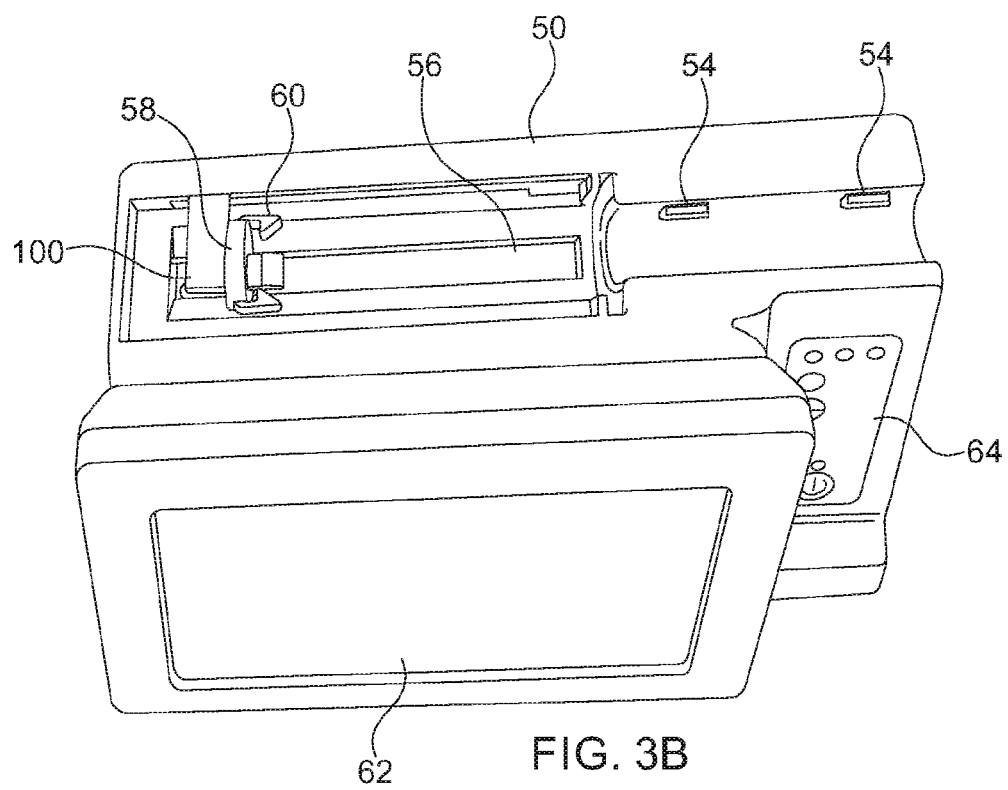
FIG. 3B is a view similar to FIG. 3A of the unit without the disposables assembly.
Figure 4:
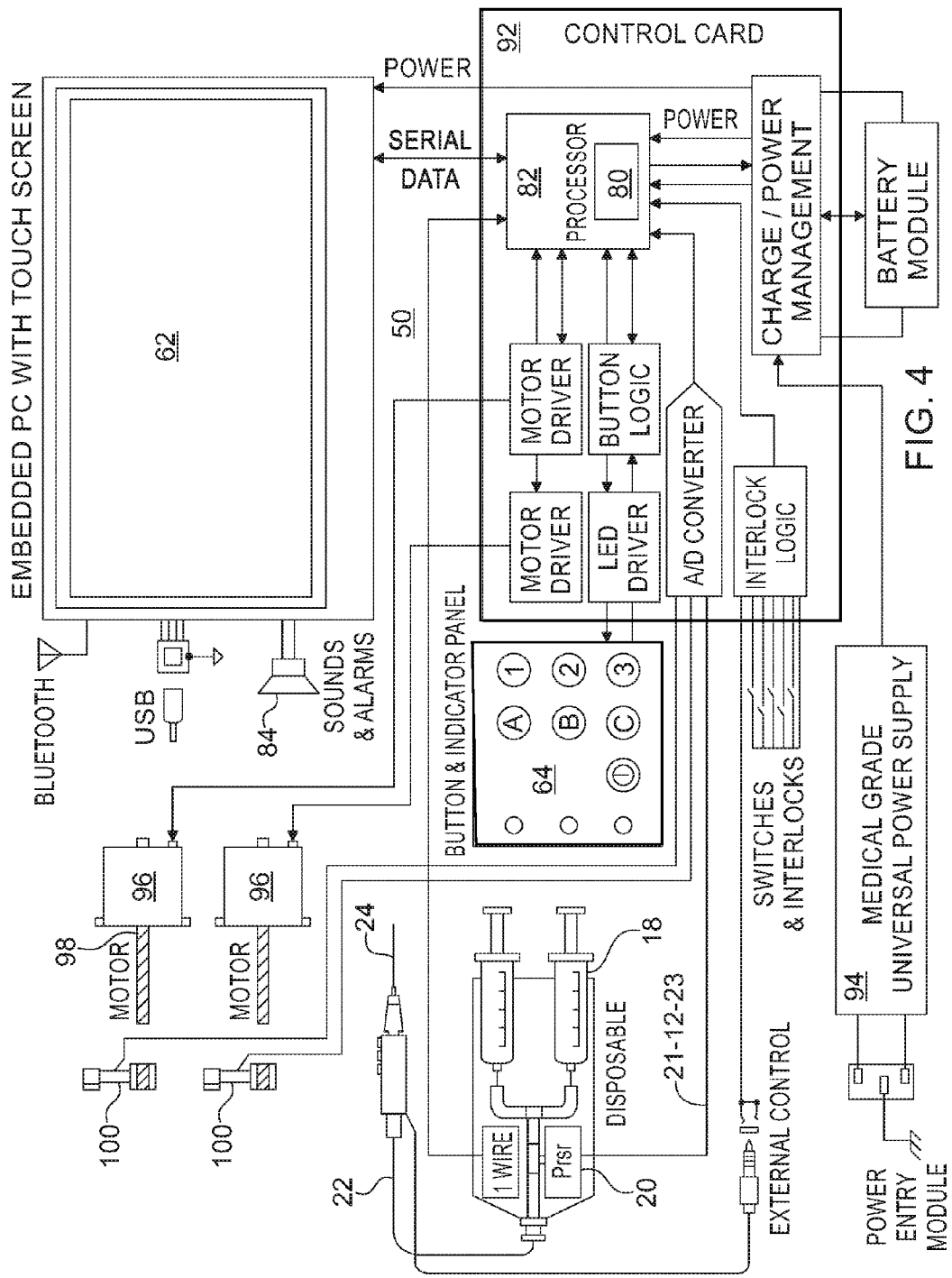
FIG. 4 is a schematic representation of one embodiment of the computer-controlled drug delivery system of the invention.

As described above, the injection device that is exemplified by the drive unit 50 in FIGS. 3A, 3B and 4, uses a non-continuous fluid-flow by continuously monitoring a pressure using the electronic pressure-transducer 20, that is preferably the pressure of the fluid during injection. Based on a pre-determined pressure that is set by the practitioner and stored in a memory 80 of a microprocessor or computer 82 of the electronics in unit 50, fluid-flow will stop, and based on a pre-determined pressure fluid-flow, will resume. It is possible that the same pre-determined pressure is used for both of these settings. In such case the pressure will build as fluid initially enters the tissue to a pre-determined level and then stop when the pressure drops below this pre-determined level. Thereafter fluid-flow will resume creating a non-continuous fluid flow.

The system has defined pre-determined levels of pressure to enable fluid-flow into targeted tissue sites while limiting the flow of drugs into non-targeted tissues. This enables a clinician to selectively inject drugs into specific sites and intended tissues for diagnostic and therapeutic procedures. Preselected maximum allowable pressure limits and/or flow rates are stored in memory 80 and define either the maximum recommended pressures that patients usually tolerate, or other criteria. As the pressure approaches this limit, a visual and/or audible and/or tactile alarm is generated for the clinician, i.e. on screen 62 and via speaker 84 that is activated by data from the microprocessor 82. In addition, data descriptive of the whole injection process is stored for future analysis in memory 80, as discussed above.

The system when in use is composed of the drive unit 50 and the disposable set-up components. The drive unit 50 houses the microprocessor or CPU 82, electronic circuitry board 92, a power supply 94 and electronic motor or motors 96 (since in the embodiment of FIG. 4, two syringes can be accommodated). Each electronic motor 96 rotates a spiral shaft 98 that moves a syringe armature 100 in a forward and reverse direction. The syringe armature 100 contains a load cell sensor to detect force. Armature 100 is connected to the stage 58 to move the stage in either direction. As also mentioned, the disposable set-up 10 comprises the Identification-Connection component 12, syringe 18, in-line pressure transducer 20, tubing set 22 and needle 24.

An exemplary method for administering an epidural injection follows. Further details of the preparation of devices for administering an epidural injection are described in WO/2014/007949. These principles and methods may be easily adapted for injections into tissues and anatomical areas other than the epidural space.

The fluid storage device is filled and a setup process is initiated during which the clinician places a preloaded syringe into the syringe receptacle on the top of the instrument. The clinician can change the fluid flow rate and peak pressure to be dispensed. Then the clinician operates a touch-screen activation and/or pneumatic control, such as a foot pedal to initiate the fluid flow. Alternatively, commands may be initiated by the clinician either electronically or by voice commands. During dispensing, the output from the transducer is used to calculate the current fluid pressure. If this pressure approaches a certain threshold, the fluid flow rate is automatically stopped to prevent excessive injection of drugs into the non-targeted tissues, thereby ensuring that the patient does not suffer undue pain or damaged to tissues from excess fluid-flow. Several optional features are also provided including aspiration, purging or charging the media with or without air.

Throughout the process, the clinician may be provided sensory feedback about the ongoing process, including but not limited to: the current flow rate, total volume ejected or aspired, total volume remaining, tissue pressures, entry pressures and other parameters. The clinician is provide with sensory feedback as to specific pre-determined pressure threshold of a first and second pressure value and sensory signals that are reflective that the motor is active or inactive during operation of the device. The slave microprocessor receives commands from the master microprocessor and generates the drive signals required to operate the motor.

More specifically, in preparation for using the unit 50, and with reference to FIGS. 3A and 3B, a disposables assembly is removed from its sterile packaging and the pre-filled body of syringe 18 is pressed into a semi-cylindrical syringe cradle 52 defined in the upper surface of the housing of unit 50 as shown in FIGS. 3A and 3B. The syringe body 18 is held firmly in place in cradle 52 by a pair of spring-loaded clamps 54 and is kept from moving axially in the cradle 52 by having its finger flange 90, that extends for the top end of syringe 18, engaged within a correspondingly shaped finger flange recess 55. The plunger 70 of syringe 18, that is in its fully extended, syringe-full location shown in FIG. 3A, is received in a plunger recess 56 in the upper surface of the unit housing, and is sized amply long, wide and deep to contain and suspend the plunger 70 without contacting it so the plunger can be pressed into the syringe body without obstruction.

A movable stage 58 with three spring-loaded thumb flange catches or hooks 60 that are pivotally mounted to the stage 58, is movable under computer control along the plunger recess 56. As will be explained more fully below, the stage 58 is moved to the right in FIGS. 3A and 3B, until the stage 58 is close enough to a thumb flange 72 of syringe 18, to allow facing beveled surfaces of the three hooks 60 to engage the thumb flange 72 form the bottom and its opposite sides, to spread under the continued movement of stage 58, and then snap closed below the thumb flange 72. A sensor in unit 50 then senses resistance to the further movement of stage 58, and the stage stops. Since, at this point, the plunger 70 is effectively axially fixed to the stage 58 by the engagement of the catches 60 on thumb flange 72, any further rightward to leftward movement of the stage 58 will also move the plunger 70 to the right, i.e. to expel fluid form the syringe body, or to the left to aspirate fluid back to the syringe body.

The pressure sensor 20 of the assembly is plugged to the proprietary connector 12 and connector 12 is plugged to the unit 50 via a jack.

Detailed Description of Operational Sequence

The top view of the instrument shows the recessed cavity 52 and recess 56, together called the syringe cradle, which allows the proper positioning to receive a standard 20 cc syringe 18. Contained within the plunger recess 56 is the movable armature 100 and stage 58 that engages the thumb pad or flange 72 of the disposable syringe 18. The mechanism that engages the thumb pad of the syringe has the series of spring loaded hook 60, which automatically capture the syringe thumb pad.

As the thumb pad 72 is engaged, the spring loaded hooks 60 will move outward, over and then engage the thumb pad in hook-like fashion. This action will secure the thumb pad, allowing the syringe stage 58 to mechanically move the syringe plunger 70 in either direction, thus ensuring that aspiration can be performed. Additionally a force sensor is integrated into the design of the syringe armature 100. The syringe armature 100 uses optical and mechanical features to identify the position of the syringe and can calculate the volume of fluid present within the syringe.

Step 1: The drive unit 50 is turned "On" via a separate side-panel that includes "On/Off", "Start/Stop", "Purge", and "Aspiration On/Off" buttons and Battery Indictors. The "On/Off" button powers up the drive unit and touch screen interface LCD 62. Turning on power automatically moves the syringe armature mechanism 100 to be in a "home" position shown in FIG. 3B.

In FIG. 3B the syringe armature 100 with moving syringe stage 58 with the auto-engage-aspiration thumb-pad receptacle 52, 56 is connected to the movable syringe armature, located on the top of the drive unit.

The top of the drive unit shows feature design, i.e. a syringe cradle, that is designed with detents or clamps 54 on the surface. These detents 54 engage the surface of the barrel of the syringe 18 with an interface as the syringe is placed within the syringe cradle to cause a temporary locking of the syringe into the syringe cradle.

Step 2: The drive unit 50 requires the use of a series of disposable components. As mentioned the disposable set-up comprises of the following system components.

A syringe 18—the preferred embodiment uses a standard 20 cc syringe from Becton Dickinson, Inc. The design is not limited to a particular size or volume syringe. The operator will load the syringe with fluid from an appropriate sterile container, such as a multi-dose drug vial or single-use glass ampule. The operator may fully load the syringe or partially load the syringe as the auto-detection feature determines the volume of drug that is contained within the syringe.

The preferred embodiment uses the in-line pressure transducer 20—such as the Meritrans® in-line pressure transducer from Merit Medical, South Jordan, Utah. It is anticipated that the force sensor in the syringe armature could provide information as to fluid pressure and negate the need for a secondary pressure sensor.

A subcutaneous hollow-bore needle 24—in the preferred embodiment a Touhy needle such as the Becton Dickinson® 20 G×3.5" Touhy Needle. Becton Dickinson, Franklin Lakes, N.J.

Sterile tubing set 22—48" arterial pressure tubing, such as ICU Medical, Inc. San Clemente, Calif.

Identification-Disposable Connector (ID-Connector) 12—the ID-Connector is a proprietary component. It verifies that an appropriate syringe, tubing set, in-line pressure sensor and needle as recommended by the manufacturer of the invention are connected to the drive unit. In the preferred embodiment the ID-Connect is permanently affixed to the pressure sensor and tubing-set and provided as a single component. It is also possible that the invention includes all disposable elements provided in a distinct kit, allowing the operator to connect the ID-Connector to the individual components for use.

The ID-Connector is then connected to the drive unit via a removable connection plug, such as the RJ-11 plug The ID-Connector communicates to the CPU of the drive unit to provide information related to the disposable. In the preferred embodiment the ID-Connector limits the number of cycles the drive unit can operate with the disposable set. This may limit usage based on physical cycling of the drive-unit and/or by measured time. Additionally, it prevents re-use of previously used or non-sterile disposables providing patient safety. The ID-Connector also ensures the proper selection of the disposable components. In the preferred embodiment the ID-Connector is rigidly connected to as many disposable components as possible, i.e. by glue, heat or chemical bonding to the in-line pressure sensor and tubing set. This is, however, not necessary for the unit to function properly.

It is anticipated that additional information may be encrypted into the ID-Connector such as, but not limited to:
  i. Drug information such as Drug Name and Formulation, Drug Manufacturer, Lot Number;
  ii. Information related to the disposables assembles;
  iii. Information related to expiration of dates for drug;
  iv. Information related to sterility of disposable kit; and
  v. Date and time the ID-Connector was used.

In a preferred embodiment, a 20 cc syringe 18 is connected to the Meritans pressure transducer 20 with attached ID-Connector and 48" Arterial Pressure Tubing set 22. At the distal end of the tubing set a Touhy (hollow-bore) needle 24 is connected.

Step 3: After the syringe 18 is inserted in the Syringe-Receptacle, the operator will view an initial screen 62 on the Drive Unit 50 stating "Load Syringe and Press Continue". Touch screen interface 62 allows the operator to touch the "Continue" button which enables the Auto-Engage-Aspiration-Receptacle to make contact with the syringe thumb-pad. The Drive-Unit can detect and confirm that the proper disposables have been inserted into the instrument through a series of features. The confirming design features include:
(1) A unique Identification Detector-Connector (ID-Connector)—that is able to communicate with the CPU confirming that the proper disposable assembly has been selected and attached to the Drive-Unit. If the ID-Connector detects an improper selection of disposable assembly or an attempt to Re-Use a disposable assembly, the Drive-Unit will prevent further operation and display a warning message and/or make an audible signal. The ID-Connector also can limit the number of cycles performed with a given disposable set-up. The ID-Connector controls the system and functions directly and/or indirectly through the CPU. Information is passed to/from the connector in both directions and therefore the CPU can store or alter the content and information on the ID-Connector during operation.
(2) The Auto-Syringe-Detection feature utilizes retention hooks of the Auto-Engaging-Aspiration-Receptacle to verify that the proper size syringe is selected. Confirmation is established by the size of the syringe thumb pad and the diameter between the hooks of the Auto-Engaging-Aspiration-Receptacle. If the syringe size and receptacle size are mismatched the hooks cannot engage. The loaded syringe is first detected through a load cell contained drive unit syringe-armature. Forward motion of the syringe-armature is automatically stopped once resistance is detected on the syringe thumb-pad. The syringe-armature will then reverse direction after the spring-activated hooks engage the syringe thumb-pad. In the preferred embodiment, when a smaller diameter syringe thumb-pad is used for a syringe size other than a 20 cc syringe the engaging hooks will not engage and a syringe will not be detected. A warning message is displayed or signal made and further use of the drive-unit is prevented. It is anticipated that different dedicated syringe sizes could be incorporated into specific designs, for example a 10 cc syringe or 5 cc syringe.
b. The Auto-Syringe-Detection feature also determines the volume of fluid within a syringe by an optical and or mechanical sensor. The volume is displayed.
c. Once detection of the syringe is completed and confirmed the system can automatically purge an appropriate amount of fluid into the tubing set to fully charge the disposable.
d. 3. In the preferred embodiment the Auto-Purge feature is activated after the Auto-Syringe-Detection feature. This ensures that the proper syringe is installed in the syringe receptacle. It is possible to change a global setting so that Auto-Purge does not occur, in which case a manual-purge option can be used from contacting the touch-screen. It may also be possible to by-pass purging altogether. By-passing "Auto-Purge" and "Manual Purge" is an option when a syringe disposable set up is used multiple times on the same patient, in which case the tubing set would have already been charged from the first purge cycle performed.

On the far right of the touch screen is a series of touch-tab's that can be assessed at any time during operation.
a. 1—"Patient" screen: Allows patient/doctor information to be input.
b. 2—"Locate" screen: Active injection screen that shows a visual
c. display of Flow Rate and of fluid pressure during the injection process thereby enabling the operator to locate the target. P1 and P2 values are noted on the screen as well.
d. 3—"Settings" screen: Allows the flow rate and pressure values, P1 value and P2 pressure value to be changed. Screen brightness, Audio-Sound Volume to be selected. Additional features include "Calibrate Touch" touch screen sensitivity and Set Date and Time, Auto-Purge On/Off.
e. 4—"Data" screen: Allows review, electronic transfer and printing of data collected during previous Locate Injection performed.

Patient screen is accessed by touching the "Patient" tab on the right of the screen. Note that the operator can switch between any screen during operation by simply touching the "tab" on the right of the screen.

Touching the "Patient" tab displays a screen through which the operator can input patient and doctor data that will be recorded with a time and date for the patient.

A further, 'settings', screen displays the following user adjustable settings:

a. "Brightness" to allow the screen to be made brighter or darker. Once selected the screen will default to that value in the future.

b. Audio-Volume adjustment to adjust the sound level during operation.

c. Calibrate Touch to adjust the sensitivity of the touch screen to accommodate for operators using barriers and/or gloves.

d. Set Date and Time to adjust the date and time.

e. Flow-Rate value to adjust the rate selected.

There is also a 'data' screen that displays patient information and physician information and retains a record of the location and injection event. This information can be stored on a removable medium and/or directly printed to a printer from the drive unit.

A 'locate' screen provides essential information during the location and injection process of the procedure.

This is the "Locate" mode active screen is viewed during operation. The following touch-screen features can be accessed directly from this screen:

i. "Start"/"Stop" button to start the flow and stop the flow of fluid manual.
 ii. "Tare Pressure" feature: Allows the system to subtract erroneous pressure reading do to altitude or height discrepancies between the patient and the instrument.
 iii. "End Treatment" will return the user to the Purge Window to reload either a new syringe set up for a new patient or allow a second syringe to be used on the same patient.
 iv. "Volume Remaining" is viewed as a graphic image of a syringe. As the fluid is expressed the graphic picture changes to reflect the change in volume showing in the visual.
 v. "Pressure" is provided in mm/Hg in real-time during operation.
 vi. Flow-rate volume that is being used.
 vii. Visual Graph displaying the pressure reading in a graph format.
 viii. Audible Sound reflecting the Pressure and Flow of the fluid.
 ix. "Print"—the operator can print the data and supporting graph from this screen.
 x. Time and Date are displayed on the screen.
 xi. Scrolling Graph—representing the majority of the screen shows a visual representation of the Flow-Rate and Pressure data being recorded. This same information is provided to the user in an Audible tone or signal so that the operator does not have to necessarily view the screen at all times.

By way of non-limiting example, the following methodology may be employed when using a device of the invention after it has been set up as described above:

1) After preparing the system for use, the clinician starts the drive unit by actuating an input mechanism, such as a foot pedal, push button or touch screen. In response to the actuation, the drive unit displaces the syringe stage 58 to start a pre-set flow rate. Sound Type-1 (e.g. a warble) is generated to indicate the motor is running. The needle is advanced slowly so that the pressure sensing capability of the system enables the detection of subtle changes in pressure as the needle is advanced. The pace of advancement of the needle should be approximately 1 cm per 3 seconds. This can be identified from laser etched markings that may be on the epidural needle that may be marked in 1 cm increments.
 2) If a false-LOR occurs before a first predetermined pressure threshold P1 is reached, the "success warning" is not sounded. The instrument automatically disregards the false-LOR by continuing to maintain the initial flow-rate. The sound type remains Type-1 throughout.

If the high pressure threshold P1 is not detected through the procedure the needle is withdrawn and re-inserted to follow a new trajectory.

3) In one embodiment the P1 threshold is used to control flow ate. As the pressure exceeds 80% of P1 the flow-rate is reduced by 50%. When the pressure exceeds P1 the motor stops. At this stage a P1 audible "warning announcement", for example "High Pressure" may be generated. Furthermore, when the motor stops after P1 is initially reached, Sound Type-2 (e.g. a flute tone) is emitted until the pressure falls below P1. In response to the pressure falling below P1, and the motor starts again. At this time Sound Type-1 starts again.

The benefit of stopping fluid flow above P1 is that this limits the quantity of fluid to be injected during the process of identification of the fluid filled tissue space. This is an improvement over the prior art since it prevents continuous flow of fluid into tissues which may have many adverse consequences.

If the pressure does not drop below threshold P2 after this point, typically the needle is withdrawn and re-inserted on to follow a new trajectory.

4) As the needle is advanced a sudden and sharp drop of pressure may occur and the pressure may pass through the second pre-determined pressure value P2. As the pressure drop below the P2 value a warning announcement is given (e.g. "Low Pressure") and a sound type changes to a Sound Type-3 (e.g. Triple Tone). Sound Type-3 is heard irrespective of the fluctuation up or down of pressure as long as it stays below the P2 value.

In response to reaching P2, the user instantaneously stops the advancement of the Touhy needle at this location.

5) A three to five second observation period is to be performed in which the pressure is to be maintained below this second predetermined value during this 3 to 5 second period of time. If the pressure plateaus or continues to decrease during this period of time this is confirmation and representative of the True-LOR and identification of the epidural space.
 6) If during the 3 to 5 second observation period the pressure raises above the second predetermined pressure value the acoustic sound of the second predetermined pressure value is discontinued indicating the needle has moved from the original position of the epidural space. Noting that the needle is no longer in the epidural space or that the needle was unintentionally advanced and the needle tip is in contact to the dura and therefore the needle should be withdrawn immediately and the procedure should be re-initiated to locate and maintain the position of the needle within the epidural space prior to discontinue the use of the device described herein.

Figure 2:
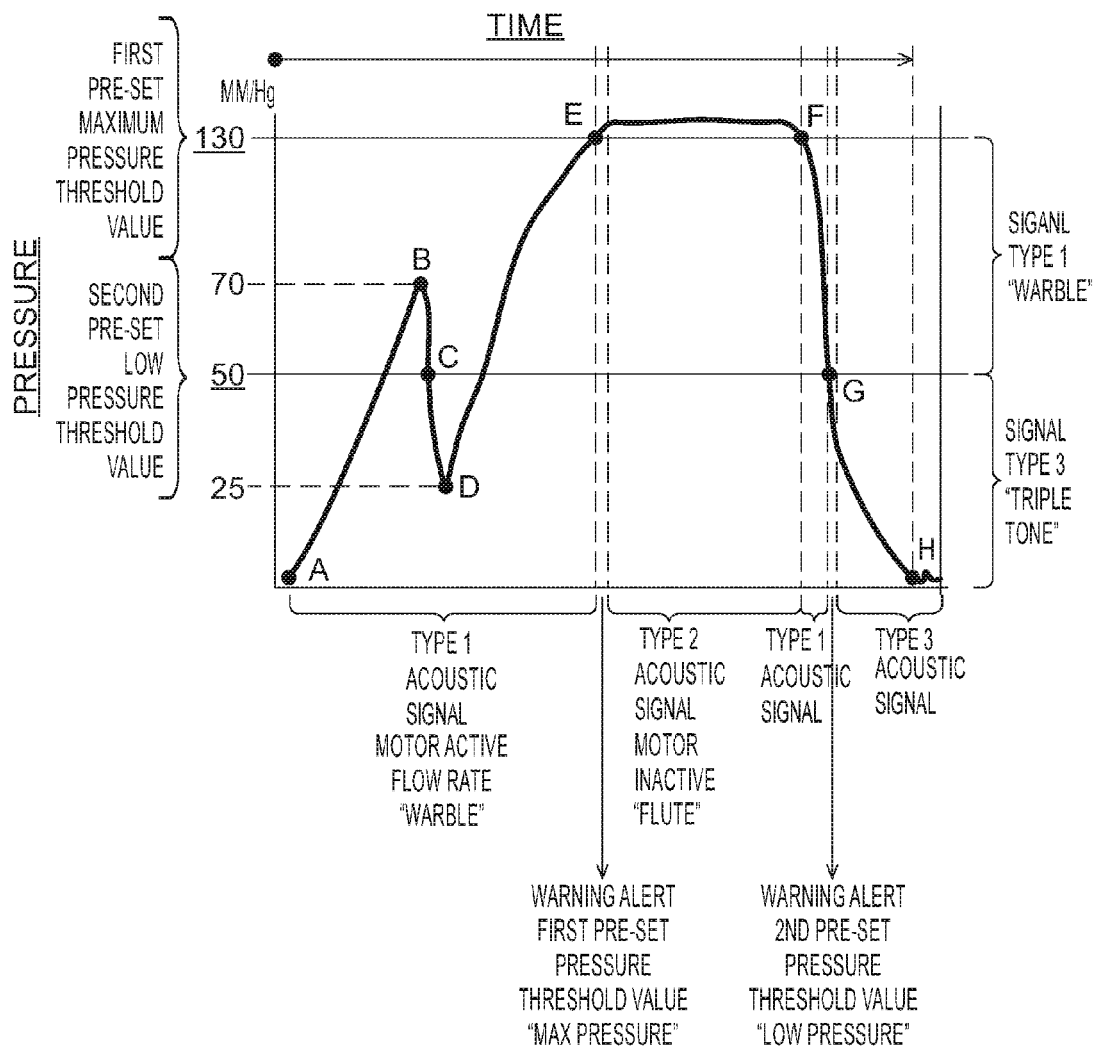
FIG. 2 shows a hypothetical time-pressure profile based on use of one embodiment of the invention described herein, annotated to show the occurrence of the different acoustic alerts, and other key events, at time points A-H.

The operation of one embodiment of the system can be understood by reference to the points A-H in FIG. 2

Point A—Device is started and needle advancement is initiated.

Points A to B: The Touhy Epidural Needle is slowly advanced forward into the patient tissues. The motor is active and a flow of fluid occurs at a specified flow-rate. The acoustic sound representative of an active motor with a flow-rate is Type-1 acoustic sound, a repeated, for example, "Warble"-type sound is emitted to inform the operator that the motor is active and there is a flow of fluid, this represents the first motor active sound type.

From Point A to Point B the pressure values increase, as seen in FIG. 2 from zero to 70 mm/Hg for this example on the screen of the instrument, and the exit-pressure values are visually displayed continuously and in real-time from Point A to Point B on the screen of the device. However, the same acoustic sound "Warble" or other tone is repeated to reflect that the motor is running.

From Point B to Point D the needle continues to be advanced until a rapid and sudden drop of pressure occurs. The visual display on the device displays a drop of pressure from 70 mm/Hg to 25 mm/Hg in this example. The acoustic sound type remains sound Type-1, the same acoustic "Warble" or other sound tone continues to be emitted, although a transition point has occurred at Point B as the pressure is now decreasing rapidly. This sound type is representative that the motor is running and there is a flow of fluid at a specific flow-rate irrespective of the changing pressure.

From Point D to Point E the needle continues to be advanced through the tissues. At Point D the pressure rebounds from the 25 mm/Hg value and rapidly increases to Point E. A transition point has occurred at Point D as the pressure is now rapidly increasing, however, the same acoustic "Warble" or other sound tone continues to be emitted. This sound type is representative that the motor is running and there is a flow of fluid at a specific flow-rate irrespective of the now rapidly increasing pressure.

NOTE: From Point A to Point E the acoustic sound, whether "Warble" or other, that is emitted represents that the motor is running at a specific flow-rate, irrespective of the changes in the pressure values.

Point E represents the First Pre-determined High Pressure Threshold Value (P1). At the instant the pressure crosses the First Pre-determined high pressure threshold value (set at 130 mm/Hg in this example) a first warning announcement is emitted with the spoken words "Max Pressure". In this embodiment it is stated one time, however, in other embodiments it is conceivable that it is repeated or a different spoken word is used such as "High Pressure" or some other term and/or sound. As the pressure ascends above this First Pre-Set High Pressure Threshold Value the motor will stop being active as the pre-set high pressure has been obtained. The logic of the software will now set a software flag in the logic such that when the subsequent Second Pre-Set Low Pressure Threshold Value (P2) is crossed a second audible warning announcement will be emitted (represented at Point G).

From Point E to Point F the motor is inactive. The operator is informed that fluid flow has occurred. Visually the graph becomes a horizontal line and the real-time continuous pressure data is displayed on the screen. An acoustic sound Type-2 is emitted to represent that the motor is not active and there is no flow of fluid. This sound type in this embodiment is, for example, a "flute" sound tone repeated between Point E and Point F.

The needle is continued to be advanced through the tissues.

From Point F to Point G a rapid and sudden drop of pressure occurs which starts at Point F (the high pressure threshold value). During this rapid and sudden drop in pressure the motor becomes active again and a flow of fluid is re-initiated, which is represented on the display of the device in the graph as well as the pressure values displayed on the screen. However, the same acoustic "Warble" or other sound tone is restarted and emitted for the operator to hear. This sound type is representative that the motor is now running and there is a flow of fluid at a specific flow-rate irrespective that the pressure is rapidly decreasing.

Point G represents the Second Pre-Set Low Pressure Threshold Value. As the pressure drops below the Second Pre-Set Low Pressure Value, 50 mm/Hg in this example, the second warning announcement is emitted with the spoken words "Low Pressure" spoken in this embodiment, stated one time. Alternatively, this audible signal may be repeated more than once or a different spoken word may be used such as "Epidural Space" or some other spoken term and/or acoustic sound to provide an objective instruction to the user.

From Point G to Point H, as the first condition was previously met which required the high pressure to be first reached to set the software flag, the subsequent drop of pressure below the Second Pre-Set Low Pressure Threshold Value becomes active to enable a new sound type to be emitted once the pressure drops below the second pre-set low pressure value. The graph displays the graph with the continued decrease in pressure and continuous real-time pressure values displayed. The acoustic sound type represents a third acoustic sound, a "Triple Tone" or other sound is emitted, representative that the Second Pre-Set Low Pressure Threshold Value has been crossed and that the motor is active and fluid is flowing. If the pressure remains below Point G the same sound type is emitted, thereby representing that the motor is running, fluid is flowing and not correlated to pressure changes below Point G.

In one embodiment, the clinician may reset the pre-determined maximum allowable pressure once the fluid-filled space is penetrated and the injection has begun. As noted above, prior to needle entry into the epidural space, the fluid pressure is high so that little or no fluid is being delivered. Upon entry of the fluid-filled space the pressure drops eventually to about 1-10 mm/Hg. This drop in pressure initiates the flow of fluid from the injection device.

It should be understood that the example of 130 mm/Hg as the pre-determined maximum pre-set pressure for stoppage of fluid flow is an example and that either a lower or higher pre-set pressure may be selected at the discretion of the clinician. Also, the second pre-determined 50 mm/Hg pressure value at which fluid flow resumes is an example and that either a lower or higher pre-set pressure may be selected at the discretion of the clinician and is merely illustrative. The principles and techniques may be modified for an injection into almost any anatomical location. What is of particular importance in this embodiment of the method and device is the ability to define and select pre-determined values of pressure to produce a non-continuous flow of drug for diagnostic and therapeutic administration.

The techniques described herein are equally applicable to human and animal tissues.

While the invention has been described with reference to several particular embodiments, it is to be understood that these embodiments are merely illustrative of the principles of the invention. Accordingly, the embodiments described in particular should be considered as exemplary, not limiting, with respect to the following claims.

Any sub-titles herein are included for convenience only, and are not to be construed as limiting the disclosure in any way.

The disclosure of all references cited herein, inasmuch as it may be used by those skilled in the art to carry out the invention, is hereby specifically incorporated herein by cross-reference.

The invention claimed is:

1. An apparatus for locating a target region which is situated in a body of a subject, comprising:
    a reservoir for receiving an injection fluid, wherein the reservoir comprises a connector for connecting the reservoir with a needle to be inserted into the body of the subject;
    a sensor for detecting a characteristic indicative of the fluid pressure in the needle;
    signal generator for supplying a true loss of pressure signal to an operator that indicates when the needle is present in the target region, wherein the true loss of pressure signal is acoustic, visual or tactile;
    a fluid controller configured to control the flow of fluid from the reservoir;
    a central controller connected with the sensor for receiving signals from the sensor and differentiating between a false loss of pressure and a true loss of pressure indicative of the needle being placed in a target area of interest, wherein the central controller is operable to control the signal generator;
    wherein the central controller differentiates between a false loss of pressure and a true loss of pressure by declaring a true loss of pressure only if two required conditions are both met, wherein the two required conditions are: (i) receipt of a signal from the sensor indicative of a first pressure threshold being exceeded; and (ii) receipt of a subsequent signal from the sensor indicative of the pressure falling below a second pressure threshold;
    wherein in response to determining a true loss of pressure, the central controller controls the signal generator to provide the true loss of pressure signal.

2. The apparatus of claim 1 wherein the first pressure threshold is characteristic of a barrier tissue which must be encountered by the needle prior to arriving at the target region and the second pressure threshold is characteristic of the target region and the second threshold is lower than the first pressure threshold.

3. The apparatus of claim 1 wherein the reservoir comprises a syringe barrel and the fluid controller comprises a syringe plunger.

4. The apparatus of claim 1 wherein the central controller is configured to control the fluid controller in response to signals received from the sensor.

5. The apparatus of claim 4 wherein the central controller is configured to control the fluid controller to stop the flow of fluid in response to receipt of a signal indicative of the first pressure threshold being exceeded.

6. The apparatus of claim 1 wherein the central controller is configured to control the signal generator to provide a second signal as long as the central controller receives a signal from the sensor indicative of the first pressure threshold being exceeded.

7. The apparatus of claim 1 wherein the central controller is configured to require a third condition in order to control the signal generator to provide the success signal, wherein the third condition is receipt of the subsequent signal for a time period exceeding a threshold.

8. The apparatus of claim 1 wherein the success signal is audible.

9. The apparatus of claim 1 wherein the sensor comprises a pressure transducer for generating a real time pressure signal corresponding to an instantaneous pressure at the point of the needle.

10. An apparatus for locating a target region which is a fluid-filled anatomic space situated in a body of a subject, wherein a barrier tissue is pierced to access the anatomic space, wherein the apparatus is configured to cooperate with a reservoir for receiving an injection fluid, a needle in fluid communication with the reservoir, and a sensor operable to detect a characteristic indicative of the fluid pressure in the needle, wherein the apparatus comprises;
    a signal generator for supplying a success signal to an operator that indicates when the needle is present in the target region, wherein the success signal is acoustic, visual or tactile; and
    a central controller operable to control the signal generator in response to signals received from the sensor;
    wherein the central controller is operable to control the signal generator to provide the success signal if three required conditions are met, wherein the three requirements are:
        (i) receipt of a signal from the sensor indicative of a first pressure threshold being exceeded;
        (ii) receipt of a signal from the sensor indicative of the pressure falling below a second pressure threshold after the first pressure threshold has already been exceeded; and
        (iii) receipt of one or more signals from the sensor indicative of the pressure remaining below the second pressure threshold for a time period that is greater than one second.

11. The apparatus of claim 10 comprising a connector for electrically connecting the central controller with the sensor.

12. The apparatus of claim 11 comprising a fluid controller that is operable to control the flow of fluid from the reservoir, wherein the central controller is configured to provide signals to the fluid controller to control the fluid controller.

13. The apparatus of claim 10 wherein the central controller is operable to control the flow of fluid from the reservoir in response to signals received from the sensor.

14. The apparatus of claim 10 wherein the first pressure threshold is characteristic of the barrier tissue which must be encountered by the needle prior to arriving at the target region and the second pressure threshold is characteristic of the target region and the second threshold is lower than the first pressure threshold.

15. The apparatus of claim 10 wherein the reservoir comprises a syringe barrel and the fluid controller comprises a syringe plunger.

16. The apparatus of claim 10 wherein the central controller is configured to control the fluid controller in response to signals received from the sensor.

17. The apparatus of claim 16 wherein the central controller is configured to control the fluid controller to stop the flow of fluid in response to receipt of a signal indicative of the first pressure threshold being exceeded.

18. The apparatus of claim 10 wherein the central controller is configured to control the signal generator to provide a second signal as long as the central controller receives a signal from the sensor indicative of the first pressure threshold being exceeded.

19. The apparatus of claim 10 wherein the time period is 3-5 seconds.

20. The apparatus of claim 10 wherein the success signal is audible.

21. The apparatus of claim 10 wherein the sensor comprises a pressure transducer for generating a real time pressure signal corresponding to an instantaneous pressure at the point of the needle.

22. An apparatus for locating a target region which is a fluid-filled anatomic space situated in a body of a subject, wherein a barrier tissue is pierced to access the anatomic space, wherein the apparatus is configured to cooperate with a reservoir for receiving an injection fluid, a needle in fluid communication with the reservoir, and a sensor operable to detect a characteristic indicative of the fluid pressure in the needle, wherein the apparatus comprises;
   a signal generator for supplying a plurality of signals to an operator in response to signals from the sensor, wherein the signals acoustic, visual or tactile; and
   a central controller operable to control the signal generator in response to signals received from the sensor;
   wherein the central controller is operable to control the signal generator to provide
      (a) a first signal in response to receipt of a signal from the sensor indicative of pressure below a first threshold;
      (b) a second signal in response to receipt of a signal from the sensor indicative of pressure above the first threshold;
      (c) a third signal in response to receipt of a signal from the sensor indicative of the pressure falling below a second threshold after receiving a signal from the sensor indicative of the pressure exceeding the first threshold.

23. The apparatus of claim 22 wherein the central controller is operable to control the signal generator so that:
   the first signal is invariable as the pressure varies as long as the pressure remains below the first threshold;
   the second signal is invariable as the pressure varies as long as the pressure remains above the first threshold; and
   the third signal is invariable as the pressure varies as long as the pressure remains below the second threshold.

24. The apparatus of claim 22 wherein the signal generator is operable to provide a first alert signal when the central controller receives a signal from the sensor that the pressure first exceeds the first threshold.

25. The apparatus of claim 24 wherein the signal generator is operable to provide a second alert signal when the central controller receives a signal from the sensor that the pressure first falls below the second threshold after first exceeding the first threshold.

26. An apparatus for locating a target region which is situated in a body of a subject, comprising:
   a reservoir for receiving an injection fluid, wherein the reservoir comprises a connector for connecting the reservoir with a needle to be inserted into the body of the subject;
   a sensor for detecting a characteristic indicative of the fluid pressure in the needle;
   signal generator for supplying a true loss of pressure signal to an operator that indicates when the needle is present in the target region, wherein the true loss of pressure signal is acoustic, visual or tactile;
   a central controller connected with the sensor for receiving signals from the sensor and differentiating between a false loss of pressure and a true loss of pressure indicative of the needle being placed in a target area of interest, wherein the central controller is operable to control the signal generator;
   wherein the central controller differentiates between a false loss of pressure and a true loss of pressure by declaring a true loss of pressure only if three required conditions are met, wherein the three required conditions are:
      (i) receipt of a signal from the sensor indicative of a first pressure threshold being exceeded;
      (ii) receipt of a subsequent signal from the sensor indicative of the pressure falling below a second pressure threshold; and
      (iii) receipt of one or more signals from the sensor indicative of the pressure remaining below the second pressure threshold for a time period that is greater than one second.

27. The apparatus of claim 26 comprising a fluid controller for controlling the flow of fluid from the fluid reservoir, wherein the central controller is configured to control the fluid controller to stop the flow of fluid in response to receipt of a signal indicative of the first pressure threshold being exceeded.

28. The apparatus of claim 27 wherein the central controller is configured to control the signal generator to provide a second signal as long as the central controller receives a signal from the sensor indicative of the first pressure threshold being exceeded.

29. The apparatus of claim 26 wherein the sensor comprises a pressure transducer for generating a real time pressure signal corresponding to an instantaneous pressure at the point of the needle.

* * * * *